(12) United States Patent
Ma et al.

(10) Patent No.: US 10,894,756 B2
(45) Date of Patent: Jan. 19, 2021

(54) METHOD FOR CATALYTICALLY HYDROGENATING OXALATES

(71) Applicant: Tianjin University, Tianjin (CN)

(72) Inventors: Xinbin Ma, Tianjin (CN); Yue Wang, Tianjin (CN); Dawei Yao, Tianjin (CN); Jing Lv, Tianjin (CN); Yujun Zhao, Tianjin (CN); Shengping Wang, Tianjin (CN)

(73) Assignee: Tianjin University, Tianjin (CN)

( * ) Notice: Subject to any disclaimer, the term of this patent is extended or adjusted under 35 U.S.C. 154(b) by 0 days.

(21) Appl. No.: 16/628,986

(22) PCT Filed: Mar. 26, 2018

(86) PCT No.: PCT/CN2018/080544
§ 371 (c)(1),
(2) Date: Jan. 6, 2020

(87) PCT Pub. No.: WO2019/011005
PCT Pub. Date: Jan. 17, 2019

(65) Prior Publication Data
US 2020/0140359 A1 May 7, 2020

(30) Foreign Application Priority Data

Jul. 13, 2017 (CN) .......................... 2017 1 0571590
Jul. 13, 2017 (CN) .......................... 2017 1 0572107

(51) Int. Cl.
| | | |
|---|---|---|
| *C07C 29/149* | (2006.01) | |
| *B01J 21/08* | (2006.01) | |
| *B01J 35/08* | (2006.01) | |
| *B01J 35/10* | (2006.01) | |

(52) U.S. Cl.
CPC .............. *C07C 29/149* (2013.01); *B01J 21/08* (2013.01); *B01J 35/08* (2013.01); *B01J 35/1019* (2013.01); *B01J 35/1042* (2013.01); *B01J 35/1061* (2013.01)

(58) Field of Classification Search
CPC ........ C07C 29/149; C07C 67/32; B01J 21/08; B01J 35/08; B01J 35/1019; B01J 35/1042; B01J 35/1061; B01J 35/1038; B01J 21/185; B01J 27/22; B01J 35/0013; B01J 37/10; B01J 37/088; B01J 37/18; B01J 37/0201; B01J 37/035; B01J 23/72
See application file for complete search history.

(56) References Cited

U.S. PATENT DOCUMENTS

| | | | |
|---|---|---|---|
| 7,563,457 B2 | 7/2009 | Cha et al. | |
| 2003/0082237 A1 | 5/2003 | Cha et al. | |
| 2010/0179356 A1* | 7/2010 | Liu ........................ | B01J 23/745 568/864 |
| 2013/0123550 A1* | 5/2013 | Ma .......................... | B01J 23/80 568/864 |

FOREIGN PATENT DOCUMENTS

| | | | | |
|---|---|---|---|---|
| CN | 101757915 A | | 6/2010 | |
| EP | 0 907 262 A2 | * | 1/1984 | ............. C07C 31/20 |
| WO | 03062372 A2 | | 7/2003 | |

OTHER PUBLICATIONS

Wang et al. ("One-pot synthesis of nanotube-based hierarchical copper silicate hollow spheres", Chem. Comm. 2008, vol. 27, pp. 6555-6557.*
Lin et al. ("Cu/SiO2 hybrid catalysts containing HZSM-5 with enhanced activity and stability for selective hydrogenation of dimethyl oxalate to ethylene glycol", Applied Catalysis A:General, 445-446, Aug. 2012, pp. 287-296).*
He et al. ("Effect of boric oxide doping on the stability and activity of a Cu-SiO2 catalyst for vapor-phse hydrogenation of dimethyl oxalate to ethylene glycol", Journal of Catalysis, 277, 2011, pp. 54-63).*
Ye et al. ("One-Pot Synthesis of Cyclodextrin-Doped Cu-SiO2 Catalysts for Efficient Hydrogenation of Dimethyl Oxalate to Ethylene Glycol", ChemCatChem, 9, 2017, pp. 4587-4597).*
Yongqiang Wang, et al.; "One-pot Synthesis of Nanotube-based Hierarchical Copper Silicate Hollow Spheres"; Chem. Commun.; Nov. 11, 2008; pp. 6555-6557; The Royal Society of Chemistry; London, U.K.
International Search Report; International Pat. Appl. No. PCT/CN2018/080544 dated Jun. 22, 2018; 4 pages.; International Searching Authority, State Intellectual Property Office of the P.R. China; Beijing, China.

(Continued)

*Primary Examiner* — Rosalynd A Keys
(74) *Attorney, Agent, or Firm* — Andrew D. Fortney; Central California IP Group, P.C.

(57) ABSTRACT

The invention discloses a method for catalytically hydrogenating oxalates. In the method, an oxalate and hydrogen gas are contacted with a nanotube assembled hollow sphere catalyst, to produce a product comprising glycolate or glycol. The predominant chemical components of the catalyst include copper and silica, in which the copper is in an amount of 5 to 60% by weight of the catalyst, and the silica is in an amount of 40-95% by weight of the catalyst. The catalyst has a specific surface area of 450-500 m²/g, an average pore volume of 0.5-1 cm³/g, and an average pore diameter of 5-6 nm. The catalyst is in a structure of assembling nanotubes on hollow spheres, wherein the hollow spheres have a diameter of 50-450 nm, and a wall thickness of 10-20 nm, and the nanotubes, vertically arranged on the surfaces of the hollow spheres, have a diameter of 3-5 nm, and a length of 40-300 nm. Even in the case of a low H₂/DMO feeding ratio, the method of the invention still can exhibit an excellent activity of hydrogenating oxalates and an excellent selectivity to ethylene glycol, and reduce circulation quantity of hydrogen gas, thereby to save power costs and apparatus costs, and it can flexibility adjust the selectivity of ethylene glycol and glycolate. Thus, the method has high industry prospects and application values.

5 Claims, 5 Drawing Sheets

(56) References Cited

OTHER PUBLICATIONS

Xinbin Ma et al.; "Nano-structured Cu/SiO2 Catalysts for Ester Hydrogenation Systems"; Abstract Book of the 30th Annual Academic Meeting of the Chinese Chemical Society, Thirty-third session: Green Chemistry; Jul. 1, 2016.

* cited by examiner

METHOD FOR CATALYTICALLY HYDROGENATING OXALATES

TECHNICAL FIELD

The invention is in the technical field of catalytic hydrogenation processes, and particularly it relates to a method for catalytically hydrogenating oxalates.

BACKGROUND ART

Ethylene glycol, as an important chemical raw material or solvent, is widely used in productions of polyester and downstream products thereof, antifreeze, lubricating oil and the like, and it has a broad market prospect. A process for preparing ethylene glycol by producing dimethyl oxalate (abbreviated as DMO) from syngas via carbon monoxide coupling reaction and then hydrogenating the dimethyl oxalate has the characteristics of high atom economy, mild reaction conditions, high product selectivity, and environmental protections, and it is one of important methods for synthesizing ethylene glycol via a non-petroleum route. Therein, hydrogenation of dimethyl oxalate is the core of the process. The other types of oxalates, such as diethyl oxalate or dibutyl oxalate, after being hydrogenated, can also produce ethylene glycol while accordingly producing the byproducts ethyl glycolate or butyl glycolate.

A copper-based catalyst can achieve good activity and selectivity in the reaction system. However, the problems of a high hydrogen to ester ratio (i.e., the molar ratio of hydrogen gas to dimethyl oxalate $H_2/DMO$) as required by the reaction feed and difficult controls of product distributions still cannot be effectively solved. At present, greatly excess hydrogen gas is required in the feed of the dimethyl oxalate hydrogenation reaction (the $H_2/DMO$ molar feed ratio is generally between 80 and 200) to obtain a yield of ethylene glycol of higher than 90%. However, in industrial applications, such a high hydrogen to ester ratio will result in an increased circulation quantity of hydrogen gas and increased requirements on parameters of associated apparatus such as a compressor, thereby to greatly increase apparatus costs and power costs required by the process. Therefore, designing a novel highly active copper-based catalyst is the key of optimizing the process technique for preparing ethylene glycol with syngas, so that the dimethyl oxalate hydrogenation reaction can achieve a high selectivity and a high yield of ethylene glycol under the condition of a low hydrogen to ester ratio.

The present invention is aimed to solve the above problems.

SUMMARY OF THE INVENTION

The invention provides a method for catalytically hydrogenating an oxalate. In the method, the oxalate and hydrogen gas are contacted with a nanotube assembled hollow sphere catalyst, to produce a product comprising glycolate or ethylene glycol. The predominant chemical components of the catalyst include copper and silica, wherein the copper is in an amount 5-60% by weight of the catalyst, and the silica is in an amount 40-95% by weight of the catalyst. The catalyst has a specific surface area of 450-500 $m^2/g$, an average pore volume of 0.5-1.0 $cm^3/g$, and an average pore diameter of 5-6 nm; the catalyst is in a structure of assembling nanotubes on hollow spheres, wherein the hollow spheres have a diameter of 50-450 nm, and a wall thickness of 10-20 nm; the nanotubes, vertically arranged on the surfaces of the hollow spheres, have a diameter of 3-5 nm and a length of 40-300 nm.

The term "silicon oxide spheres" herein only is an abbreviation name for a person skilled in the art, and it actually means "silica spheres". Hence, in the patent, the term "silicon oxide spheres" is synonymous to the term "silica spheres".

Preferably, the copper is in an amount 10-40% by weight of the catalyst, and the silica is in an amount of 60-90% by weight of the catalyst.

Preferably, the catalyst has a specific surface area of 460-470 $m^2/g$, an average pore volume of 0.7-0.8 $cm^3/g$, and an average pore diameter of 5.1-5.5 nm.

Preferably, the hollow spheres have a diameter of 200-350 nm, and a wall thickness of 10-15 nm.

Preferably, the nanotubes have a diameter of 3.5-4 nm, and preferably a length of 180-230 nm.

Preferably, the nanotube assembled hollow sphere catalyst comprising nanotubes having a length of 40-65 nm, more preferably 40-60 nm, is used so that the selectivity of glycolate in the product can reach 84%-100%.

Preferably, the nanotube assembled hollow sphere catalyst comprising nanotubes having a length of 110-300 nm is used so that the selectivity of ethylene glycol in the product can reach 85-98%.

Further preferably, when using the nanotube assembled hollow sphere catalyst of the invention, even under the conditions that the molar ratio of hydrogen gas to oxalate may be as low as 20, i.e. $H_2/DMO \geq 20$, the reaction temperature is from 160 to 220° C., the reaction pressure is from 1.5 to 3 MPa, and the liquid weight hourly space velocity is from 0.5 to 5H$^-$, the yield of ethylene glycol can still be higher than 95%. Therein, the liquid weight hourly space velocity refers to the weight space velocity of the oxalate.

The nanotube assembled hollow sphere catalyst itself and the method for preparing it are known in the prior art, for example, see Wang Y, et al., Chem. Commun., 6555-6557 (2008) and Sheng Y, et al., Chem. Mat., 27, 658-667 (2015).

One common preparing method comprises the following steps:

Step 1: A silicon source, as a raw material, is mixed with an alkaline agent and water in different volume ratios ranging from 0.13 to 1.9, to produce a ultrapure silica sphere material having a regular geometric shape and a particle size of from 50 to 450 nm at temperatures of 30-80° C. and pH values of 8.5-13.5, wherein the silicon source is sodium silicate, silica sol or tetraethyl orthosilicate; the alkaline agent is ammonia-water solution, ammonium chloride or sodium hydroxide.

Step 2: The obtained ultrapure silica sphere material is uniformly mixed with a copper precursor salt solution, and the copper, counting by the weight of metal oxide, is added in an amount of 5 to 60% by weight. The silica spheres continuously dissolve in an alkaline environment, and the copper precursor salt solution reacts with the silica spheres whilst the obtained product gradually deposits and curls to form tubular structures, the reaction product are subjected to a hydrothermal treatment for 5-30 h under alkaline conditions at hydrothermal treatment temperatures of 120-180° C. and then are dried and calcined to produce a hollow sphere nanomaterial assembled with nanotubes, which is called as a catalyst precursor. Therein, the copper precursor salt solution comprises copper acetate or copper nitrate.

Step 3: The obtained nanotube assembled hollow sphere is dried at 50 to 120° C. for 4-12 hours; then, it is calcined at 300 to 700° C. for 3-12 h in an atmosphere of air, and the flow rate of air required by the calcination for per gram of the catalyst is 6 to 150 mL/min; at last, the obtained catalyst is reduced by the means of an online in-situ reduction at temperatures of 150 to 400° C. in a reductive atmosphere of hydrogen gas or 10% hydrogen/argon mixed gas, and the flow rate of hydrogen gas required by the reduction for per gram of the catalyst is 40 to 200 mL/min. Therein, the drying method is a common drying method or a vacuum drying method.

Preferably, the silicon source is tetraethyl orthosilicate.
Preferably, the alkaline agent is ammonia-water solution.
Preferably, the copper precursor salt solution comprises copper nitrate.
Preferably, the drying method is a vacuum drying method.

In Step 1, the size of the ultra-pure silica spheres can be controlled by adjusting the volume ratio of alkaline agent to water. For example, when the alkaline agent is ammonia-water solution, and the volume ratio of ammonia-water solution to water is 0.15, ultrapure silica microspheres having a particle size of 84 nm can be obtained; when the volume ratio of ammonia-water solution to water is 0.77, ultrapure silica microspheres having a particle size of 369 nm can be obtained. Similar rules are also applicable for other alkaline agents, i.e., the higher the ratio of alkaline agent to water, the higher the diameter of obtained ultrapure silica microspheres.

In Step 2, the length of the nanotubes may be controlled by adjusting the hydrothermal treatment time. For example, when the hydrothermal time is prolonged from 5 h to 30 h, the length of the nanotubes may be extended from 63 nm to 232 nm. Basically, the longer the hydrothermal time, the longer the length of the nanotubes. However, when the copper ions or silicate ions in the solution are exhausted, basically, the length of the nanotubes will not increase as the hydrothermal time rises.

The invention has the following advantages and beneficial effects:

1. In the invention, for the first time, a nanotube assembled hollow sphere catalyst for catalyzing other reactions in the prior art are used for catalyzing the hydrogenation reaction of dimethyl oxalate, and it was unexpectedly found that the catalyst can solve the problem that the hydrogenation reaction requires a high partial pressure of hydrogen gas and a high hydrogen to ester ratio. In experiments, it was found that under the condition that the other factors, such as reaction temperature, pressure, and reaction time, are substantially the same, the method of the invention still can exhibit excellent catalytic activity and selectivity to target product (the conversion of dimethyl oxalate >98%, and the yield and selectivity of ethylene glycol each are >97%) in a low hydrogen to ester ratio ($H_2$/DMO=20), and it can render circulation quantity of hydrogen gas in need to decrease by 75%, thereby to greatly save power consumption of a gas compressor and increase processing capacity of a reactor per unit.

2. The invention can flexibly adjust the product distribution of glycolate and ethylene glycol by varying the length of the nanotubes on the hollow spheres, thereby to confer a higher flexibility to production adjustments.

3. The method of the invention has a stability of production process due to the excellent stability exhibited by the catalyst during the hydrogenation procedure.

BEST MODES FOR CARRYING OUT THE INVENTION

The present invention will be further described in detail by combining the drawings and the specific examples. It should be noted that the following examples are only illustrative, but not limited, and the invention cannot be limited by the following examples. Raw materials as used in the following examples and in the comparative examples each are commercially available, and the used alkaline agents (ammonia-water solution, ammonium chloride and sodium hydroxide) each are in a form of aqueous solution.

Example 1

Preparation of Ultrapure Silica Spheres 80 g of tetraethyl orthosilicate were weighted and dissolved in 200 ml of ethanol while stirring, to obtain a clear solution A; 132 mL of ammonia-water solution were taken to uniformly mix with 98 mL of deionized water and 86 mL of ethanol, to obtain a clear solution B; at 40° C., the two solutions A and B were mixed and stirred for 5 hour, to obtain a solution of ultrapure silica spheres with uniform surfaces that have homogenous particle sizes.

Preparation of Catalyst Precursors 18 g of trihydrated copper nitrate were weighed and, with 80 mL of ammonia-water solution, dissolved in 200 mL of deionized water, and they were mixed uniformly while stirring to obtain a clear solution. Thereafter, the solution of ultrapure silica spheres was dropwise added to the clear solution (1 drop per second) and stirred at 60° C. for 1 h, to obtain a uniformly dispersed solution. The solution, being placed in a closed container, was hydrothermally treated at 150° C. for 30 h, and after solids were separated therefrom, they were vacuum dried at 80° C. for 6 h and calcined at 500° C. for 6 h, to obtain the catalyst.

Online Reduction of Catalyst and Evaluations on Catalytic Effects

In the invention, a gas phase hydrogenation reaction of dimethyl oxalate was conducted in a fixed bed reactor. The catalyst that has been calcined was tableted and sieved to prepare particles having a size of from 40 to 60 meshes. 0.58 g of the catalyst were weighed and placed in an isothermal reactor while a 10% $H_2/N_2$ atmosphere was charged to conduct the reduction reaction at 300° C. for 4 h, and after the online reduction, the catalyst as used in the invention was obtained. After the reduction, the temperature was decreased to the reaction temperature at 190° C. Dimethyl oxalate was gasified and charged into the reactor by being mixed with hydrogen gas, and the reaction was conducted in a hydrogen to ester ratio of 20 and a weight space velocity of dimethyl oxalate (DMO) of 3 $h^{-1}$ at the pressure of 3 MPa. The product was analyzed by utilizing gas chromatography to determine the components of dimethyl oxalate (DMO), ethylene glycol (EG), methyl glycolate (MG) and ethanol (EtOH), and obtain the conversion of dimethyl oxalate and the selectivity of each product. The evaluation results of the obtained catalyst are shown in Table 1.

Figure 9:
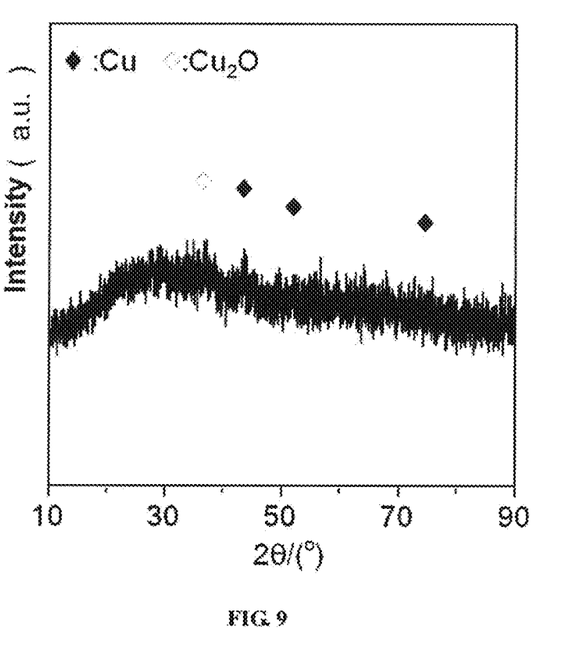
FIG. 9 is an X-ray diffraction (XRD) pattern of the nanotube assembled hollow sphere catalyst used in the invention.

The catalyst of the invention (i.e. the product after the online reduction) was also characterized by XRD. From the X-ray diffraction (XRD) pattern of the catalyst of the invention as shown in FIG. 9, it can be seen that there is a broad diffraction peak at 2θ=22°, the peak being a characteristic diffraction peak of amorphous $SiO_2$, and this shows that the silicon is present in the form of silica. The characteristic diffraction peak at 2θ=37.0 is the diffraction peak (JCPDS 34-1354) of $Cu_2O$ (111), while the characteristic diffraction peaks at 2θ=43.3°, 2θ=50.6° and 2θ=74.1° are the diffraction peaks (JCPDS 65-9743) of the metal copper (Cu). These peaks each are weak and broad, which shows that Cu and $Cu_2O$ are highly dispersed in the reduced catalyst, and the catalyst exhibits a good activity.

Comparative Example 1

Preparation of Ultrapure Silica Spheres

The method for preparation of ultrapure silica spheres is the same as that of Example 1.

Preparation of Catalyst Precursor 13 g of dehydrated copper chloride were weighed and, with 80 mL of ammonia-water solution, dissolved in 200 mL of deionized water, and they were mixed uniformly while stirring to obtain a clear solution. Thereafter, the solution of ultrapure silica spheres was dropwise added to the clear solution (1 drop per second) and stirred at 60° C. for 1 h, to obtain a uniformly dispersed solution. The solution, being placed in a closed container, was hydrothermally treated at 150° C. for 30 h, and after solids were separated therefrom, they were vacuum dried at 80° C. for 6 h and calcined at 500° C. for 6 h, to obtain the catalyst.

Evaluations of Catalyst

The method of evaluating the catalyst is the same as that in Example 1, and the results are shown in Table 1.

Comparative Example 2

Preparation of Ultrapure Silica Spheres

The method for preparation of ultrapure silica spheres is the same as that of Example 1.

Preparation of Catalyst 22 g of trihydrated copper acetate were weighed and, with 80 mL of ammonia-water solution, dissolved in 200 mL of deionized water, and they were mixed uniformly while stirring to obtain a clear solution. Thereafter, the solution of ultrapure silica spheres was dropwise added to the clear solution (1 drop per second) and stirred at 60° C. for 1 h. to obtain a uniformly dispersed solution. The solution, being placed in a closed container, was hydrothermally treated at 150° C. for 30 h, and after solids were separated therefrom, they were vacuum dried at 80° C. for 6 h and calcined at 500° C. for 6 h, to obtain the catalyst.

Evaluation of Catalyst

The method of evaluating the catalyst is the same as that in Example 1, and the results are shown in Table 1.

Comparative Example 3

Preparation of Ultrapure Silica Spheres

The method for preparation of ultrapure silica spheres is the same as that of Example 1.

Preparation of Catalyst 19 g of copper sulfate pentahydrate were weighed and, with 80 mL of ammonia-water solution, dissolved in 200 mL of deionized water, and they were mixed uniformly while stirring to obtain a clear solution. Thereafter, the solution of ultrapure silica spheres was dropwise added to the clear solution (1 drop per second) and stirred at 60° C. for 1 h, to obtain a uniformly dispersed solution. The solution, being placed in a closed container, was hydrothermally treated at 150° C. for 30 h, and after solids were separated therefrom, they were vacuum dried at 80° C. for 6 h and calcined at 500° C. for 6 h, to obtain the catalyst.

Evaluation of Catalyst

The method of evaluating the catalyst is the same as that in Example 1, and the results are shown in Table 1.

Comparative Example 4

Preparation of Ultrapure Silica Spheres

The method for preparation of ultrapure silica spheres is the same as that of Example 1.

Preparation of Catalyst 18 g of copper nitrate trihydrate were weighed and, with 80 mL of ammonia-water solution, dissolved in 200 mL of deionized water, and they were mixed uniformly while stirring to obtain a clear solution. Thereafter, the solution of ultrapure silica spheres was rapidly added (in a spout form) to the clear solution and stirred at 60° C. for 1 h, to obtain a uniformly dispersed solution. The solution, being placed in a closed container, was hydrothermally treated at 150° C. for 30 h, and after solids were separated therefrom, they were vacuum dried at 80° C. for 6 h and calcined at 500° C. for 6 h, to obtain the catalyst.

Evaluation of Catalyst

Figure 5:
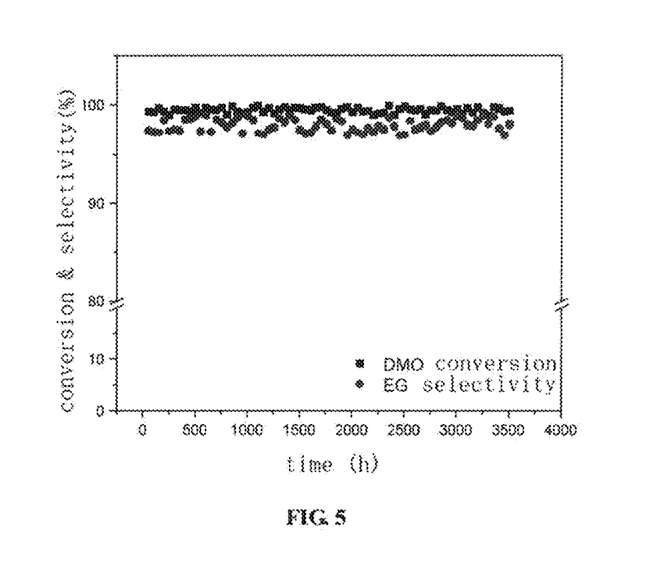
FIG. 5 is a data diagram of the lifetime of the catalysts for preparation of ethylene glycol by hydrogenating dimethyl oxalate.

The method of evaluating the catalyst is the same as that in Example 1, and the results are shown in Table 1. It can be seen that when the copper nitrate is used as the copper salt precursor and the solution of ultrapure silica spheres was dropwise added (1 drop per second), the conversion of dimethyl oxalate (DMO) can reach 100% and the selectivity of ethylene glycol (FG) is 98%. The evaluation on the stability of Example 1 is shown in FIG. 5, and it can be seen that the catalysts of the invention exhibit excellent stability.

TABLE 1

Evaluations on Catalysts Prepared by using Different Methods and Precursors

| | Copper Salt Precursors | Method for Adding Silica spheres | Cu conent/% | DMO Conversion/% | EG Selective/% |
|---|---|---|---|---|---|
| Example 1 | Copper nitrate | Adding dropwise | 20 | 100 | 98 |
| Comparative Example 1 | Copper chloride | Adding dropwise | 20 | 87 | 75 |
| Comparative Example 2 | Copper acetate | Adding dropwise | 20 | 100 | 86 |
| Comparative Example 3 | Copper sulfate | Adding dropwise | 20 | 95 | 78 |
| Comparative Example 4 | Copper nitrate | Adding rapidly | 20 | 82 | 70 |

Examples 2-5

The preparation method of the catalysts and the evaluation conditions thereof are the same as those in Example 1. By varying the amount of the added trihydrated copper nitrate, the catalysts with different copper loading quantities (S wt %, 10 wt %, 30 wt %, 40 wt %) were respectively obtained. The evaluation results are shown in Table 2, and it can be seen that when the Cu loading is greater than 20 wt %, the selectivity of ethylene glycol is higher than 90%.

TABLE 2

Performance Evaluations on Catalysts with Different Loading Quantities

| | Cu Loading Quantity wt % | DMO Conversion/% | EG Selectivity/% |
|---|---|---|---|
| Example 1 | 20 | 100 | 98 |
| Example 2 | 5 | 95 | 80 |
| Example 3 | 10 | 98 | 85 |
| Example 4 | 30 | 100 | 96 |
| Example 5 | 40 | 100 | 92 |

Examples 6-10

Figure 1:
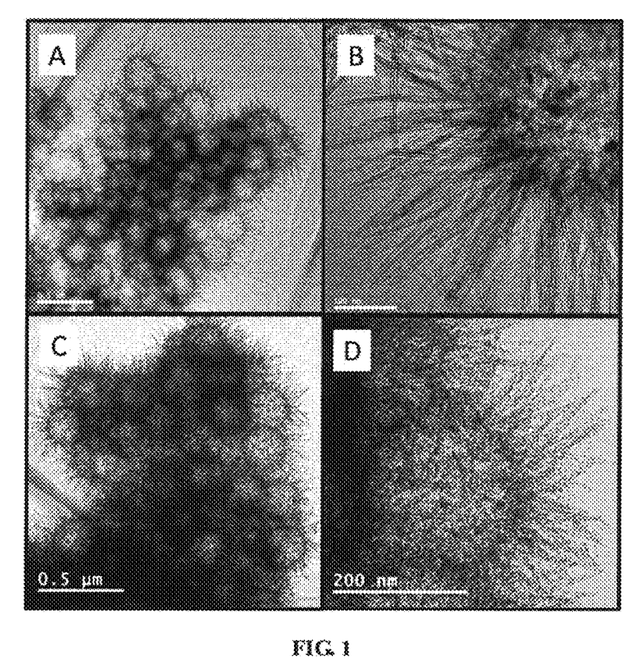
FIG. 1 shows the transmission electron micrographs of the nanotube assembled hollow sphere catalysts used in the present invention, wherein A and B are the transmission electron micrographs of the catalysts before they are reduced by $H_2$, and C and D are transmission electron micrographs of the catalysts themselves.
Figure 2:
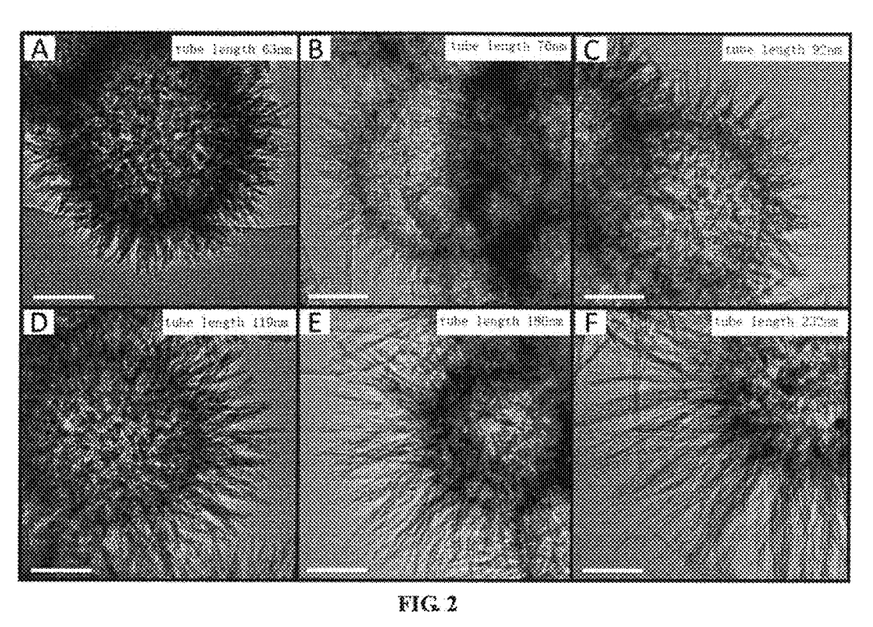
FIG. 2 shows the transmission electron micrographs of the catalyst precursors synthesized in different hydrothermal treatment time periods, wherein the hydrothermal treatment time periods are shown as follows: A: 5 h, B: 10 h, C: 15 h, D: 20 h, E: 25 h, F: 30 h; a scale: 100 nm.
Figure 3:
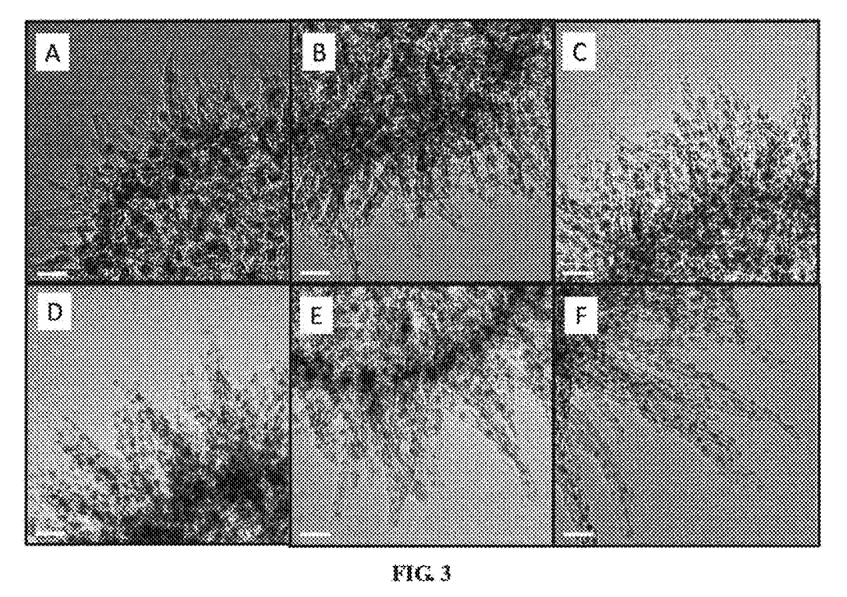
FIG. 3 shows transmission electron micrographs of the reduced catalysts obtained after reductions of the catalyst precursors shown in FIG. 2 with hydrogen gas, wherein the hydrothermal treatment time periods are shown as follows: A: 5 h, B: 10 h, C: 15 h, D: 20 h, E: 25 h, F: 30 h; a scale: 20 nm.
Figure 4:
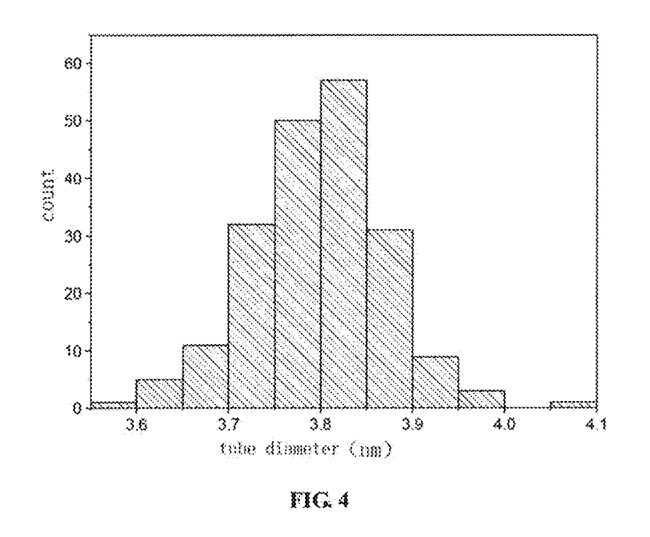
FIG. 4 is a statistical diagram of the diameters of the nanotubes of the nanotube assembled hollow sphere catalysts used in the invention.

The preparation method of the catalysts and the evaluation conditions thereof are the same as those in Example 1. By varying the hydrothermal treatment time, hollow sphere catalysts assembled with nanotubes having different lengths were respectively obtained, and the lengths of the nanotubes were determined by TEM (see FIG. 2 and FIG. 3), and the diameters of the nanotubes were shown in FIG. 4. The evaluation results of the catalysts are shown in Table 3, and it can be seen that when the length of the nanotubes in the catalysts is lower than 65 nm, the predominant product is methyl glycolate, and when the length of the nanotubes in the catalysts is greater than 110 nm, the predominant product is ethylene glycol.

TABLE 3

Performance Evaluations on Catalysts with Different Nanotube Lengths

| | Hydrothermal Treatment Time/h | Nanotube Length/nm | DMO Conversion/% | MG Selectivity/%) | EG Selectivity/%) |
|---|---|---|---|---|---|
| Example 1 | 30 | 232 | 100 | 2 | 98 |
| Example 6 | 5 | 63 | 92 | 84 | 15 |
| Example 7 | 10 | 70 | 95 | 47 | 53 |
| Example 8 | 15 | 92 | 100 | 27 | 72 |
| Example 9 | 20 | 119 | 100 | 12 | 87 |
| Example 10 | 25 | 180 | 100 | 5 | 94 |

Examples 11-14

The evaluated catalyst is the same as the catalyst in Example 1, and by varying the reaction temperature in the reaction conditions and maintaining the other conditions unchanged, examples 11-14 were obtained. The evaluation results of the catalyst are shown in Table 4, and it can be seen that when the reaction temperature is from 190 to 200° C., the selectivity of ethylene glycol obtained by the catalyst reaches 95% or above.

TABLE 4

Performance Evaluations on Catalysts at Different Reaction Temperatures

| | Reaction Temperature/° C. | DMO Conversion/% | MG Selectivity/% | EG Selectivity/% | EtOH Selectivity/% |
|---|---|---|---|---|---|
| Example 1 | 190 | 100 | 2 | 98 | 0 |
| Example 11 | 180 | 81 | 63 | 37 | 0 |
| Example 12 | 185 | 98 | 17 | 83 | 0 |
| Example 13 | 200 | 100 | 0 | 95 | 5 |
| Example 14 | 205 | 100 | 0 | 92 | 8 |

Comparative Example 5

8 g of copper nitrate trihydrate were weighed and added with deionized water to dissolve them while stirring, and thereafter, a suitable amount of 28% ammonia-water solution was slowly added to formulate a copper ammonia solution while a certain amount of deionized water was supplemented. Then, the copper ammonia solution was added with 77 g of a 30% silica sol solution and aged for 4 hours while continuously stirring. The temperature was increased to 80° C. to remove the ammonia in the solution until the pH1-6-7. By filtration, solid materials were separated, and they were dried under vacuum at 80° C. for 6 h and calcined at 500° C. for 6 h, to obtain a catalyst. The catalyst is an existing catalyst that has been reported in the prior art documents (Gong J, et al. Synthesis of Ethanol via Synthesis on Cu/SiO$_2$ Catalysts with balanced Cu$^0$—Cu$^+$ sites, Journal of the American Chemical Society 134, 13922-13925 (2012); Chen L, et al. Cu/SiO$_2$ Catalysts Prepared by the Ammonia-evaluation Method, Texture, Structure and Catalysis Performance in Hydrogenation of Dimethyl oxide to Ethylene Glycol, Journal of Catalysis 257, 172-180 (2008)). The catalyst is a conventional supported catalyst in which active sites of metal species are uniformly dispersed on internal and external surfaces of porous carriers.

Figure 6:
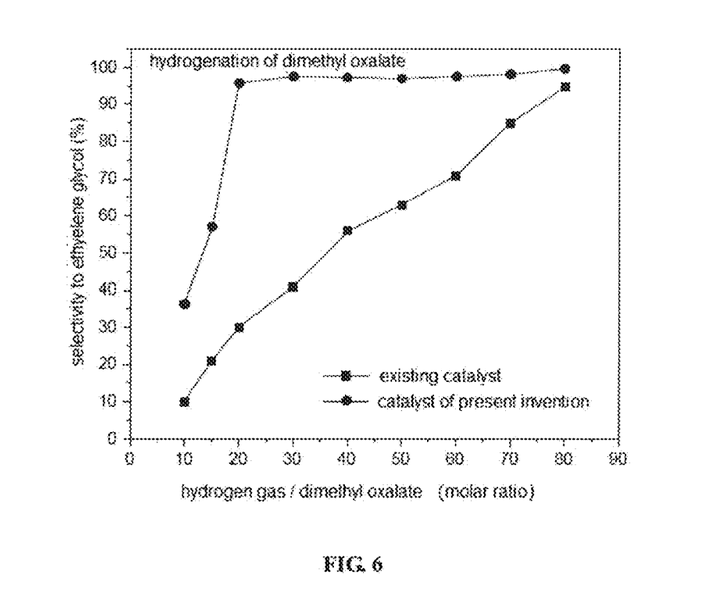
FIG. 6 is a diagram showing the performance evaluations to the catalyst of the invention and an existing catalyst in different hydrogen gas/dimethyl oxalate molar ratios, wherein the existing catalyst is $Cu/SiO_2$ catalyst as prepared by an ammonia-evaporation method, which currently has a good activity in the hydrogenation reaction of oxalates to produce ethylene glycol, see Gong J, et al. J. Am. Chem. Soc., 134, 13922-13925 (2012) and Chen J, et al. J. Catal., 257, 172-180 (2008).
Figure 7:
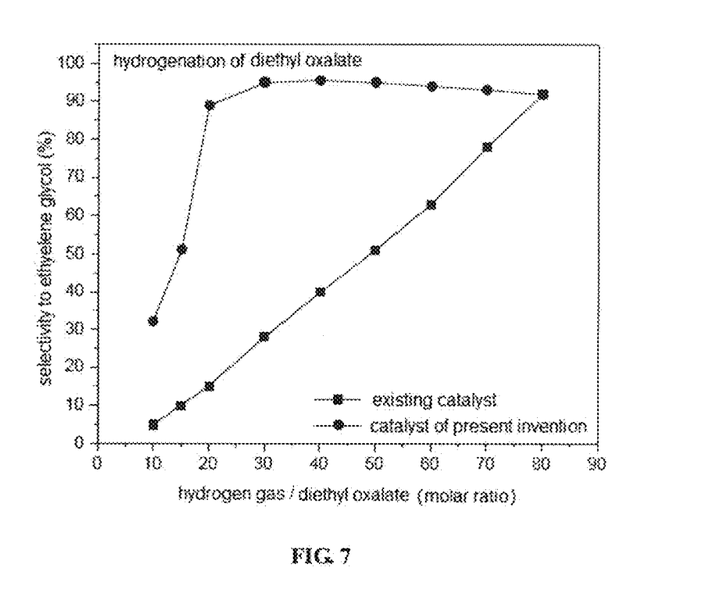
FIG. 7 is a diagram showing the performance evaluations to the catalyst of the invention and an existing catalyst in different hydrogen gas/diethyl oxalate molar ratios, wherein the existing catalyst is the existing catalyst as used in FIG. 6.
Figure 8:
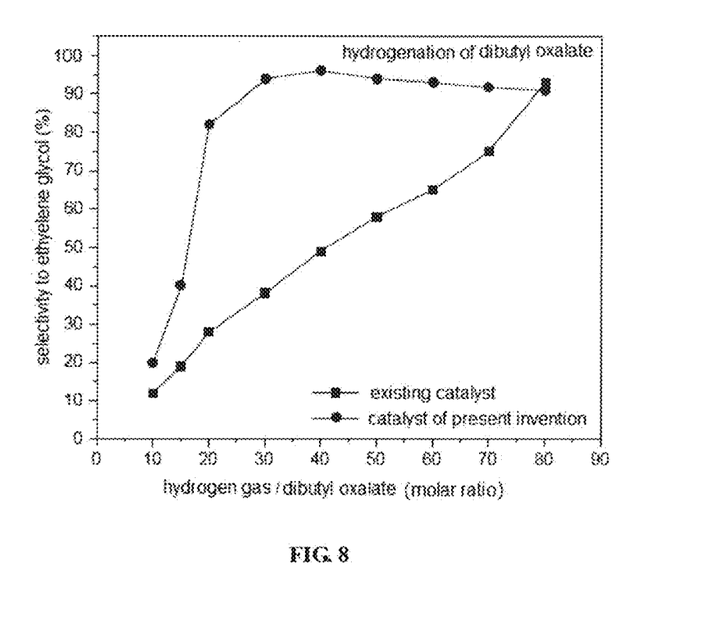
FIG. 8 is a diagram showing the performance evaluations to the catalyst of the invention and an existing catalyst in different hydrogen gas/dibutyl oxalate molar ratios, wherein the existing catalyst is the existing catalyst as used in FIG. 6.

Directed to the catalyst of the invention used in Example 1 and the existing catalyst in Comparative Example 5, in different hydrogen to ester ratios, the reaction of hydrogenating dimethyl oxalate, diethyl oxalate and dibutyl oxalate to prepare ethylene glycol was evaluated with the other conditions identical to those in Example 1. The results are shown in FIG. 6 to FIG. 8, it can be seen that for the hydrogenation of dimethyl oxalate, using the nanotube assembled hollow sphere catalyst of the invention can achieve a hydrogen to ester ratio in the raw material as low as 20 while assuring the yield of ethylene glycol to be higher than 95%, and as for the reactions of hydrogenating diethyl oxalate and dibutyl oxalate, the hydrogen to ester ratio in the raw material may be as low as 30. This demonstrates that the method of the invention can achieve unexpected technical effects.

The above contents has made illustrative depictions to the invention. It should be noted that any simple variations, modifications or other equivalent substitutions made by a person skilled in the art without paying any creative efforts fall into the protection scope of the invention.

The invention claimed is:

1. A method for catalytically hydrogenating dimethyl oxalate (DMO), characterized in that: the dimethyl oxalate and hydrogen gas are contacted with a nanotube assembled hollow sphere catalyst at a hydrogen to DMO ratio of 20, a weight space velocity of DMO of 3 h$^{-1}$ at a pressure of 3 MPa, and a temperature of 190° C. to produce a product comprising ethylene glycol at a conversion of DMO of about 100% and a selectivity of ethylene glycol of at least 98%, wherein the predominant chemical components of the catalyst include copper and silica, in which the copper is in an amount of 20% by weight of the catalyst, and the silica is in an amount of 80% by weight of the catalyst; the catalyst has a specific surface area of 450-500 m$^2$/g, an average pore volume of 0.5-1 cm$^3$/g, and an average pore diameter of 5-6 nm; the catalyst has a structure comprising nanotubes on hollow spheres, in which the hollow spheres have a diameter of 50-450 nm and a wall thickness of 10-20 nm, and the nanotubes are on surfaces of the hollow spheres and have a diameter of 3.4-4 nm and a length of 232 nm.

2. The method according to claim 1, characterized in that the catalyst has a specific surface area of 460-470 m$^2$/g, an average pore volume of 0.7-0.8 cm$^3$/g, and an average pore diameter of 5.1-5.5 nm.

3. The method according to claim 1, characterized in that the hollow spheres have a diameter of 200-350 nm and a wall thickness of 10-15 nm.

4. The method according to claim 1, characterized in that the nanotubes extend from the surfaces of the hollow spheres.

5. The method according to claim 1, characterized in that the conversion of DMO is 100%.

* * * * *